(12) United States Patent
Kibayashi

(10) Patent No.: US 9,753,269 B2
(45) Date of Patent: Sep. 5, 2017

(54) ENDOSCOPE

(71) Applicant: OLYMPUS CORPORATION, Tokyo (JP)

(72) Inventor: Takehide Kibayashi, Yamato (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/418,808

(22) Filed: Jan. 30, 2017

(65) Prior Publication Data

US 2017/0139198 A1  May 18, 2017

Related U.S. Application Data

(63) Continuation of application No. PCT/JP2015/078774, filed on Oct. 9, 2015.

(30) Foreign Application Priority Data

Oct. 17, 2014  (JP) .................. 2014-212802

(51) Int. Cl.
  *G02B 7/02*  (2006.01)
  *G02B 23/24*  (2006.01)
  (Continued)

(52) U.S. Cl.
  CPC ........ *G02B 23/243* (2013.01); *A61B 1/00045* (2013.01); *A61B 1/00114* (2013.01);
  (Continued)

(58) Field of Classification Search
  USPC ................. 359/694–704, 811–830
  See application file for complete search history.

(56) References Cited

U.S. PATENT DOCUMENTS

2009/0185032 A1* 7/2009 Sakai .................. A61B 1/00096
   348/65
2009/0303619 A1  12/2009 Iwasaki et al.
  (Continued)

FOREIGN PATENT DOCUMENTS

EP  2072001 A2  6/2009
EP  2130482 A1  12/2009
  (Continued)

OTHER PUBLICATIONS

International Search Report dated Dec. 22, 2015 issued in PCT/JP2015/078774.
  (Continued)

*Primary Examiner* — Mohammed Hasan
(74) *Attorney, Agent, or Firm* — Scully, Scott, Murphy & Presser, P.C.

(57) ABSTRACT

An endoscope includes: an endoscope distal end rigid member; an objective optical system fixing frame; a moving frame; a wire unit including a rigid shaft portion; a wire unit connecting projection portion configured such that a flange having a diameter larger than the rigid shaft portion is screwed to a distal end face side; a first wire unit insertion hole through which a flange of the rigid shaft portion can pass in a state that screwing to the wire unit connecting projection portion is canceled; a lid member; a second wire unit insertion hole configured to be coaxial with a center axis of the first wire unit insertion hole, and through which the flange of the rigid shaft portion can pass; and a sealing member.

5 Claims, 7 Drawing Sheets

(51) Int. Cl.
  *A61B 1/04* (2006.01)
  *A61B 1/06* (2006.01)
  *A61B 1/00* (2006.01)
  *G02B 7/09* (2006.01)
  *G02B 7/10* (2006.01)

(52) U.S. Cl.
  CPC ............... *A61B 1/042* (2013.01); *A61B 1/06* (2013.01); *G02B 7/09* (2013.01); *G02B 7/10* (2013.01)

(56) References Cited

U.S. PATENT DOCUMENTS

2013/0083182 A1 4/2013 Kitano
2016/0377855 A1* 12/2016 Takata ............... A61B 1/00096
                                                    359/696

FOREIGN PATENT DOCUMENTS

| JP | H11-311744 A | 11/1999 |
| JP | 2002-122795 A | 4/2002 |
| JP | 2003-290134 A | 10/2003 |
| JP | 2009-148369 A | 7/2009 |
| JP | 2009-291364 A | 12/2009 |
| JP | 2009-300761 A | 12/2009 |
| JP | 2013-075028 A | 4/2013 |

OTHER PUBLICATIONS

Japanese Office Action dated Jul. 19, 2016 issued in JP 2016-520116.

* cited by examiner

ENDOSCOPE

CROSS REFERENCE TO RELATED APPLICATION

This application is a continuation application of PCT/JP2015/078774 filed on Oct. 9, 2015 and claims benefit of Japanese Application No. 2014-212802 filed in Japan on Oct. 17, 2014, the entire contents of which are incorporated herein by this reference.

BACKGROUND OF THE INVENTION

1. Field of the Invention

The present invention relates to an endoscope including an image pickup unit in which a moving lens is moved forward and backward in an optical axis direction by pushing and pulling a wire by an operation of an operation lever in an insertion portion.

2. Description of the Related Art

An endoscope has been used in in-vivo observation and treatment or inspections and repair inside plant equipment for industrial use or the like.

In recent years, an endoscope which is provided with a mobile optical system in an objective optical system configuring an image pickup unit of the endoscope, and is capable of adjusting a focus of a photographing image or adjusting wide/tele magnification or the like has been further utilized.

In an endoscope apparatus in Japanese Patent Application Laid-Open Publication No. 2003-290134, an image pickup unit is disclosed in which a moving lens which is a variable focus lens can be moved forward and backward along an optical axis to a focused focus position by pushing and pulling an operation wire inserted into an operation portion and an insertion portion by an operation of a focus operation lever provided in the operation portion.

SUMMARY OF THE INVENTION

An endoscope as one aspect of the present invention includes: an endoscope distal end rigid member; an objective optical system fixing frame configured to hold an optical member configuring an objective optical system arranged on a distal end side inside a through-hole formed along a longitudinal axis of the endoscope distal end rigid member; a moving frame arranged on a holding frame freely movably forward and backward and configured to hold a moving lens such that the moving lens is moved forward and backward along an optical axis of the objective optical system; a wire unit including an operation wire, one end portion of which is connected to an operation lever, and a rigid shaft portion configured such that another end portion of the operation wire is integrally fixed to one end face side, a diameter of the rigid shaft portion being larger than the operation wire; a wire unit connecting projection portion provided protruding outward from an outer peripheral surface of the moving frame, and configured such that a flange provided on another end face side of the rigid shaft portion and having a diameter larger than the rigid shaft portion is screwed to a distal end face side; a first wire unit insertion hole provided on a holding frame protrusion portion including a proximal end face to which a distal end face of the wire unit connecting projection portion protruding outward from an outer peripheral surface of the holding frame comes into contact, and configured to be a through-hole through which a flange of the rigid shaft portion can pass in a state that screwing to the wire unit connecting projection portion is canceled; a lid member attached to the first wire unit insertion hole; a second wire unit insertion hole formed along the longitudinal axis of the endoscope distal end rigid member, configured to be coaxial with a center axis of the first wire unit insertion hole, and configured to be a through-hole through which the flange of the rigid shaft portion can pass in the state that screwing to the wire unit connecting projection portion is canceled; and a sealing member configured to seal the second wire unit insertion hole.

DETAILED DESCRIPTION OF THE PREFERRED EMBODIMENT(S)

Hereinafter, the present invention will be described using the drawings.

Note that, in following descriptions, the drawings based on the embodiment described below are schematic, so please keep in mind that a relation between a thickness and a width of individual parts and a ratio of the thicknesses of the respective parts or the like are different from the actual ones, and even between the drawings, a part where the relation of mutual dimensions or the ratio is different is sometimes included.

Figure 1:
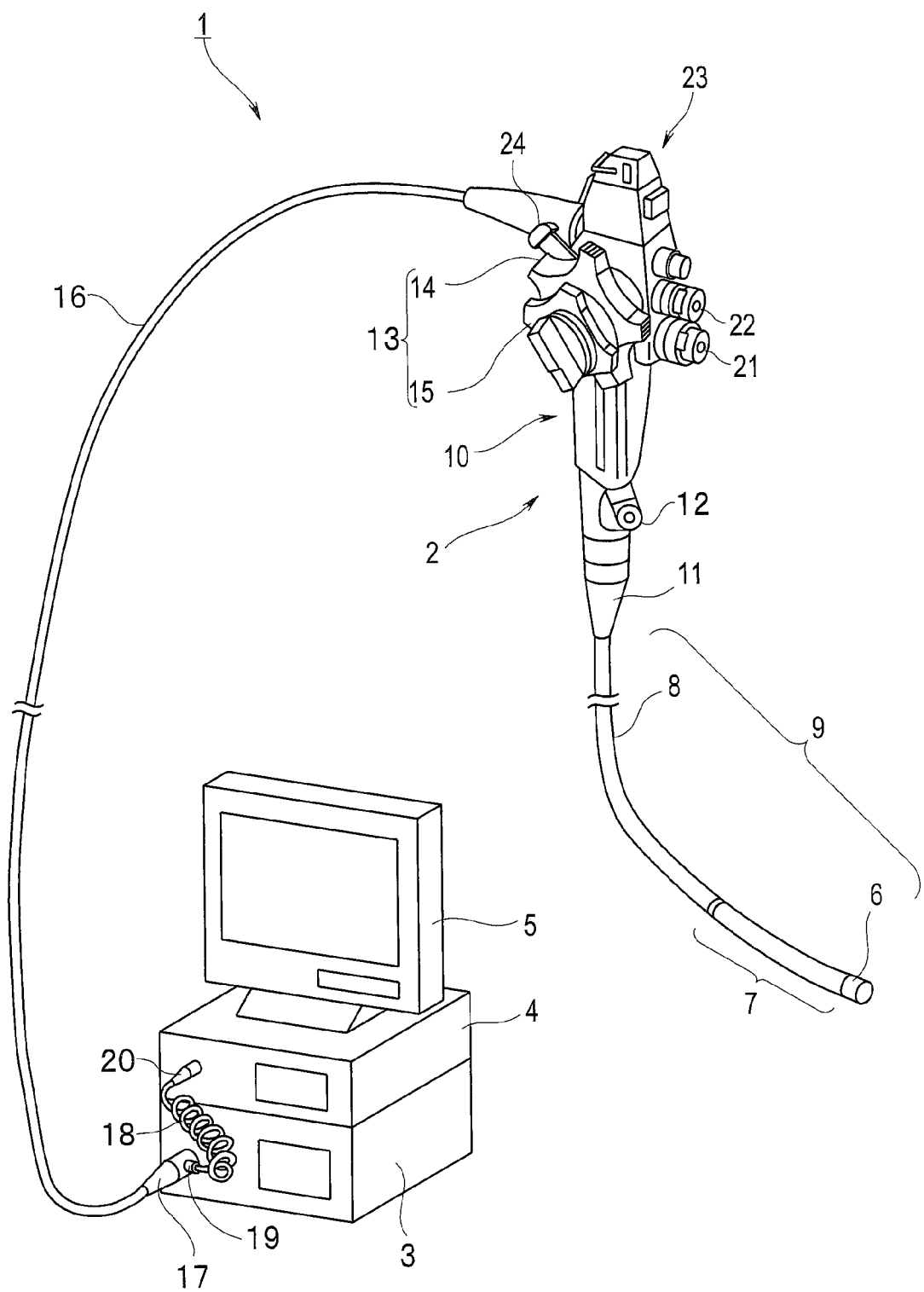
FIG. 1 is a plan view illustrating an entire configuration of an endoscope.

As illustrated in FIG. 1, an electronic endoscope system 1 of the present embodiment is mainly configured by an electronic endoscope (described as an endoscope, hereinafter) 2, a light source device 3, a video processor 4, and a color monitor 5.

The endoscope 2 includes an insertion portion 9, and an operation portion 10 provided on a proximal end side of the insertion portion 9. From a side portion of the operation portion 10, a universal cord 16 extends. On an end portion of the universal cord 16, a scope connector 17 is provided.

The scope connector 17 is freely attachable and detachable to/from the light source device 3. To/from a side portion of the scope connector 17, an endoscope side connector 19 provided on one end portion of a scope cable 18 is freely attachable and detachable. On the other end portion of the scope cable 18, a processor side connector 20 is provided. The processor side connector 20 is freely attachable and detachable to/from the video processor 4.

The insertion portion 9 is configured by connecting a distal end portion 6, a bending portion 7, and a flexible tube portion 8 in order from a distal end side. On a distal end face of the distal end portion 6, a well-known distal end opening (see a sign 6m in FIG. 2), an observation window (see a sign 6w in FIG. 2), an illumination window (not shown in the figure), a nozzle (not shown in the figure) and the like are disposed. The bending portion 7 is configured to bend in four upper, lower, left and right directions, for example.

On a back surface side of the observation window 6w, an image pickup unit including a moving lens to be described later is disposed. In addition, a distal end face of a light guide bundle not shown in the figure faces a back surface side of the illumination window. The light guide bundle transmits illumination light of an illumination lamp provided inside the light source device 3.

The operation portion 10 is provided with a bend preventer 11 which protects the proximal end side of the insertion portion 9. The operation portion 10 is provided with a treatment instrument introducing port 12. The treatment instrument introducing port 12 and the distal end opening 6m of the distal end portion 6 are mainly connected by a treatment instrument channel tube (see a sign 6c in FIG. 2) inserted and arranged inside the insertion portion 9.

The operation portion 10 is provided with a bending operation unit 13, an air/water feeding button 21, a suction button 22, a switch portion 23 configured by a plurality of switches to mainly operate an image pickup function, and an operation lever 24 or the like.

The operation lever 24 moves a moving lens frame including a moving lens forward and backward in an optical axis direction by pushing and pulling a wire unit to be described later and, for example, adjusts a focus or adjusts wide/tele magnification or the like.

The bending operation unit 13 of the present embodiment is provided with an up-down operation knob 14 and a left-right operation knob 15.

The distal end portion 6 of the insertion portion 9 of the endoscope 2 and an image pickup unit 30 provided inside the distal end portion 6 will be described with reference to FIG. 2 and FIG. 3.

Figure 2:
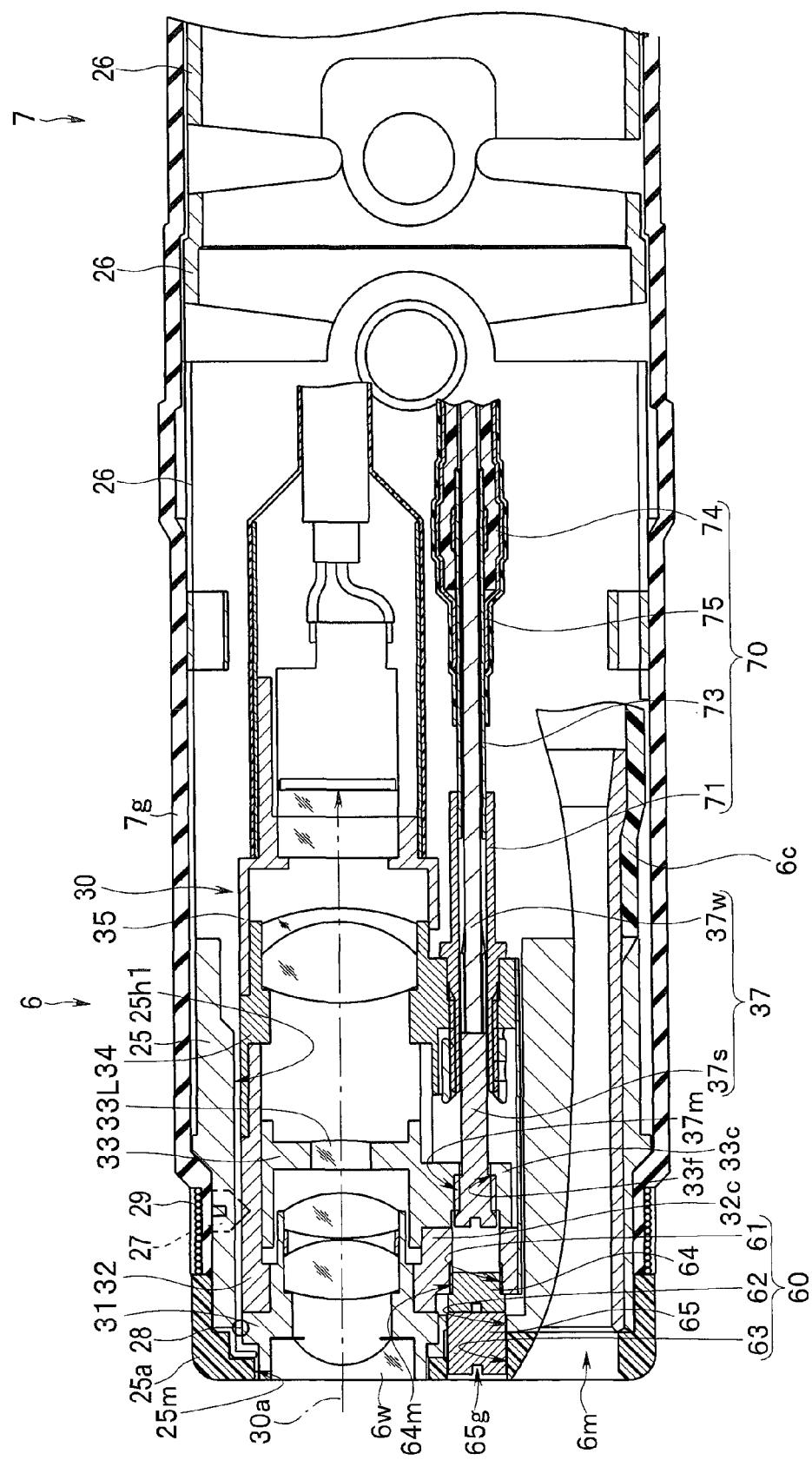
FIG. 2 is a sectional view illustrating an internal configuration of a distal end portion and a bending portion.

As illustrated in FIG. 2, the image pickup unit 30 is disposed inside the distal end portion 6. The image pickup unit 30 is arranged and fixed inside a through-hole 25h1 for image pickup optics formed in a distal end rigid portion 25 which is an endoscope distal end rigid member. A center axis of the through-hole 25h1 for image pickup optics is formed along a longitudinal axis of the distal end rigid portion 25.

The image pickup unit 30 includes a moving lens 33L moved forward and backward in the optical axis direction in an objective optical system in order to configure a focusing mechanism or a zooming mechanism.

Figure 3:
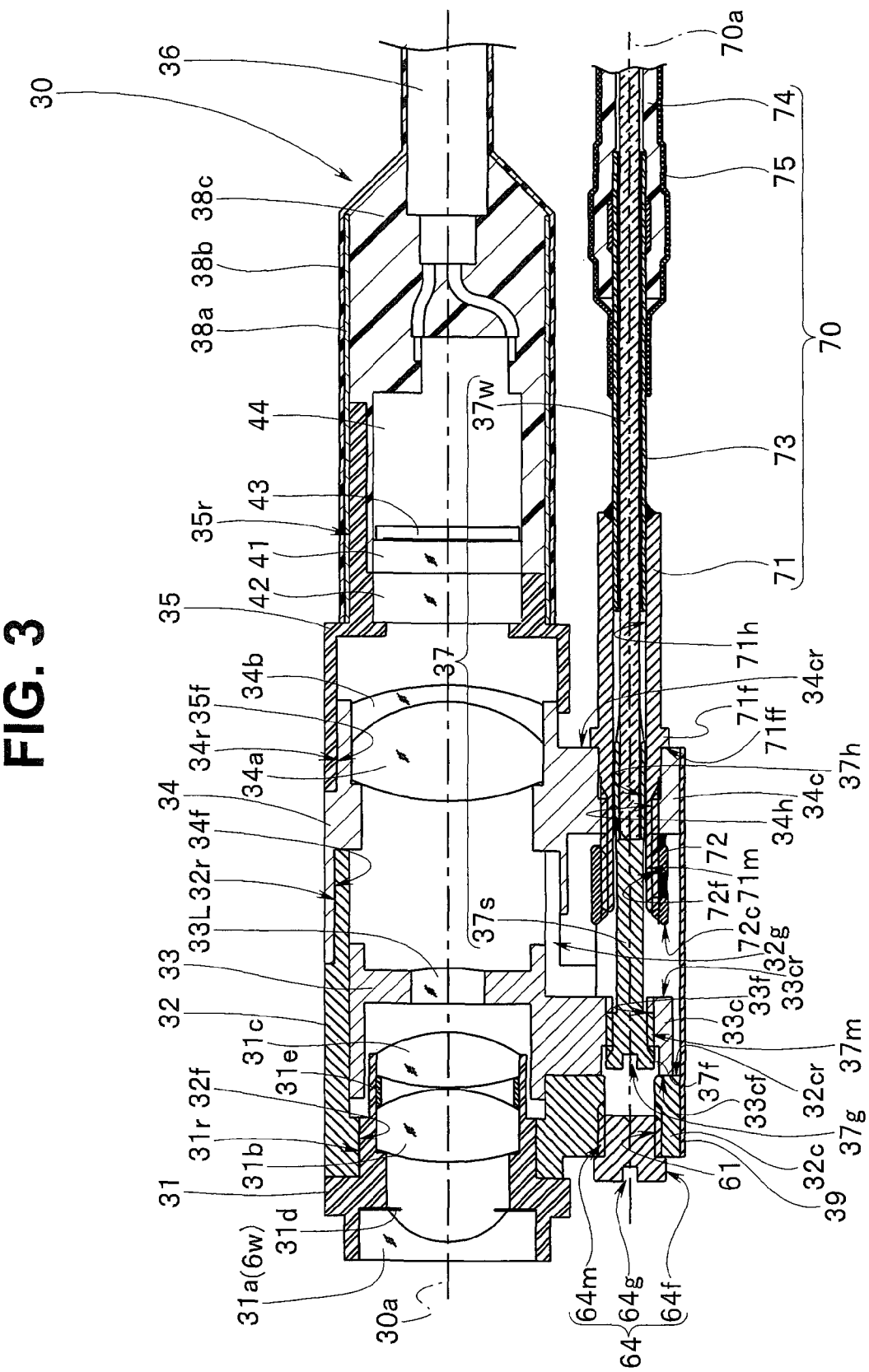
FIG. 3 is a diagram illustrating an image pickup unit.

As illustrated in FIG. 3, the image pickup unit 30 is configured mainly including a first objective lens fixing frame 31 holding a plurality of optical members, a holding frame 32, a distal end portion 32f of which is fixed to a proximal end portion 31r of the first objective lens fixing frame 31, a moving frame 33 arranged inside the holding frame 32 freely movably forward and backward and holding a moving lens 33L, a second objective lens fixing frame 34, a distal end portion 34f of which is fixed to a proximal end portion 32r of the holding frame 32, holding the plurality of optical members for example, an element frame 35, a distal end portion 35f of which is fixed to a proximal end portion 34r of the second objective lens fixing frame 34, and to which an image pickup device is disposed, a signal cable 36, and a wire unit 37.

In the present embodiment, an objective optical system fixing frame is configured by the first objective lens fixing frame 31, the holding frame 32 holding the moving frame 33, and the second objective lens fixing frame 34. The first objective lens fixing frame 31 is fixed to a side of a distal end cover 25a which is a distal end side of the through-hole 25h1 for image pickup optics.

The wire unit 37 is configured by an elongated rigid shaft portion 37s configuring the distal end side, and an elongated wire 37w extending from the rigid shaft portion 37s.

The proximal end portion which is one end portion of the wire 37w is connected to the operation lever 24 inside the operation portion 10. The distal end portion which is the other end portion of the wire 37w is disposed inside a wire fixing hole 37h provided on a proximal end face side of the rigid shaft portion 37s, and is integrally fixed by adhesion for example.

That is, an outer diameter of the rigid shaft portion 37s is larger than an outer diameter of the wire 37w.

On the distal end portion of the rigid shaft portion 37s, a distal end portion flange 37f protruding outward from a shaft portion outer peripheral surface is provided. On a distal end face of the distal end portion flange 37f, a groove 37g where a distal end of a screwdriver is to be disposed is formed. The groove 37g is a minus-shaped groove or a plus-shaped groove.

The rigid shaft portion 37s is provided with a male screw 37m. The male screw 37m of the rigid shaft portion 37s is integrally fixed by screwing the male screw 37m to a screw hole 33f formed at a wire unit connecting projection portion 33c to be described later.

The element frame 35 includes two optical members 41 and 42 such as cover glass held on an image area front surface of the image pickup device, a solid-state image pickup device chip 43 such as a CCD and a CMOS, an image area of which is positioned on a front surface, and a laminated substrate 44.

The solid-state image pickup device chip 43 and the laminated substrate 44 are electrically connected by an FPC or the like not shown in the figure. In addition, to the laminated substrate 44, a distal end of a corresponding signal line among a plurality of signal lines inserted inside the signal cable 36 is connected.

The signal cable 36 is inserted inside the insertion portion 9, the operation portion 10, the universal cord 16, and the scope cable 18, and the proximal end of the signal line is connected to the processor side connector 20.

A sign 38a denotes a metallic reinforcing frame, and the reinforcing frame 38a is fitted to a proximal end outer peripheral portion of the element frame 35. An outer periphery of the reinforcing frame 38a and a part to the distal end part of the signal cable 36 are covered with a covering member 38b which is a heat-shrinkable tube.

Inside a space formed by the reinforcing frame 38a and the covering member 38b from the proximal end part of the element frame 35, watertightness is retained, and a protective agent 38c such as an adhesive for protecting electronic components or the like is filled.

To the first objective lens fixing frame 31, an optical lens 31a which is the observation window 6w, a plurality of optical lenses 31b and 31c, a diaphragm 31d, an interval ring 31e, and the like are fixed as the plurality of optical members.

The holding frame 32 includes a holding frame protrusion portion 32c and an axial direction notched groove 32g. The holding frame protrusion portion 32c is a projection portion protruding outward from a predetermined position of an outer peripheral surface of the holding frame 32. The axial direction notched groove 32g is set to a predetermined length regarding a direction of an optical axis 30a of an objective optical system in consideration of a moving distance of the moving frame 33.

To the second objective lens fixing frame 34, optical lenses 34a and 34b for example are fixed as the plurality of optical members. The second objective lens fixing frame 34 includes a fixing frame protrusion portion 34c. The fixing frame protrusion portion 34c is a projection portion protruding outward from the outer peripheral surface of the second objective lens fixing frame 34, and the fixing frame protrusion portion 34c is provided so as to face the holding frame protrusion portion 32c.

A sign 39 denotes a dustproof cover, and is formed in a U shape. A U-shaped inner surface is watertightly fixed by adhesion to a curved surface distal end portion of the holding frame protrusion portion 32c and a curved surface distal end portion of the fixing frame protrusion portion 34c.

The moving frame 33 includes the wire unit connecting projection portion 33c. The wire unit connecting projection portion 33c is a projection portion protruding outward from the outer peripheral surface of the moving frame 33. The wire unit connecting projection portion 33c passes through the axial direction notched groove 32g, protrudes outward from the holding frame outer peripheral surface by a predetermined amount, and is arranged in an airtight space between the holding frame protrusion portion 32c and the fixing frame protrusion portion 34c covered with the dustproof cover 39.

The screw hole 33f is formed at the wire unit connecting projection portion 33c protruding from the holding frame outer peripheral surface, the male screw 37m of the rigid shaft portion 37s described above is screwed, and the flange 37f is arranged on a surface of a distal end face 33cr. In a state that the wire unit 37 is screwed and fixed to the wire unit connecting projection portion 33c, the wire unit 37 is pushed and pulled accompanying the operation of the operation lever 24, thereby moving the wire unit connecting projection portion 33c forward and backward in the optical axis direction inside the axial direction notched groove 32g.

A proximal end face 32cr of the holding frame protrusion portion 32c is a restriction surface, and a distal end face 33cf of the wire unit connecting projection portion 33c comes into contact. By the distal end face 33cf of the wire unit connecting projection portion 33c being in contact with the proximal end face 32cr of the holding frame protrusion portion 32c, the moving lens 33L of the moving frame 33 is arranged at a first position which is near the proximal end side optical lens 31c.

The holding frame protrusion portion 32c is provided with a first wire unit insertion hole 61 which is a through-hole including a center axis parallel to the optical axis 30a. The first wire unit insertion hole 61 configures a wire unit attaching/detaching hole 60 to be described later.

The first wire unit insertion hole 61 is a screw hole, and is closed by a lid member 64 being screwed and arranged. The lid member 64 is provided with a distal end portion flange 64f and a male screw portion 64m. On a distal end face of the distal end portion flange 64f, a recessed groove 64g where a distal end of a screwdriver is to be disposed is formed. The recessed groove 64g is a minus-shaped groove or a plus-shaped groove. By screwing and fixing the lid member 64 to the first wire unit insertion hole 61, an end face of the distal end portion flange 64f comes into contact with the distal end face around the first wire unit insertion hole 61, and the insertion hole 61 is closed.

The fixing frame protrusion portion 34c is provided with a guide member fixing hole 34h which is a through-hole including a center axis parallel to the optical axis 30a. Inside the guide member fixing hole 34h, a guide pipe 71 configuring a wire guide member 70 is fixed.

The guide pipe 71 is a rigid pipe member, and includes a through-hole 71h to which the rigid shaft portion 37s of the wire unit 37 is to be inserted. On a middle portion of the guide pipe 71, a flange 71f protruding outward is provided. The guide pipe 71 is fixed to the fixing frame protrusion portion 34c in the state that a distal end face 71ff of the flange 71f is in contact with a proximal end face 34cr of the fixing frame protrusion portion 34c.

In the fixed state, a male screw 71m is provided on the outer peripheral surface of the guide pipe 71 protruding from the distal end face of the guide member fixing hole 34h. To the male screw 71m, a female screw 72f of an adjustment ring 72 is screwed.

The distal end face of the adjustment ring 72 is a restriction surface 72c, and the proximal end face 33cr of the wire unit connecting projection portion 33c comes into contact. By the proximal end face 33cr of the wire unit connecting projection portion 33c being in contact with the restriction surface 72c of the adjustment ring 72, the moving lens 33L of the moving frame 33 is arranged at a second position which is near the distal end side optical lens 34a.

That is, the adjustment ring 72 is arranged at a predetermined stipulated position by appropriately adjusting a screwing amount to the guide pipe 71. The adjustment ring 72 is integrally fixed to the guide pipe 71 by applying the adhesive for example to a gap between the male screw 71m and the female screw 72f.

The wire guide member 70 includes a connection pipe 73, a wire guide tube 74, and a net tube 75, in addition to the guide pipe 71. A center axis 70a of the wire guide member 70 is parallel to the optical axis 30a.

The connection pipe 73 connects the guide pipe 71 and the wire guide tube 74. The guide pipe 71 is externally fitted, arranged and integrally fixed to the distal end portion of the connection pipe 73, and the wire guide tube 74 is externally fitted, arranged and integrally fixed to the proximal end portion of the connection pipe 73.

Inside a through-hole of the wire guide tube 74, the wire 37w is arranged freely movably forward and backward. The proximal end portion of the wire guide tube 74 is fixed to a predetermined part inside the operation portion 10. The wire guide tube 74 is a protective member that protects the wire 37w.

On the other hand, the net tube 75 is a protective member that protects the wire guide tube 74 and covers the outer peripheral surface of the wire guide tube 74. The net tube 75 is farmed in a tubular shape by braiding metallic thin wires.

As illustrated in FIG. 2, the image pickup unit 30 is arranged inside the through-hole 25h1 for image pickup optics, and is integrally fixed to the distal end rigid portion 25 by a set machine screw 27. A sign 28 denotes an O-shaped ring, and the watertightness of the inner peripheral surface of the through-hole 25h1 for image pickup optics and the distal end side outer peripheral surface of the image pickup unit 30 is retained by the O-shaped ring 28.

To the distal end face side of the distal end rigid portion 25, the distal end cover 25a is bonded and fixed. On the outer periphery of the distal end rigid portion 25 and the outer periphery of a bending piece 26 configuring the bending portion 7, bending rubber 7g is integrally put on.

The distal end side outer peripheral portion of the bending rubber 7g is fixed to the outer peripheral surface of the distal end rigid portion 25 by providing a bobbin adhesion portion 29.

The distal end cover 25a configures the distal end face of the insertion portion 9, and watertightly covers the distal end face side of the distal end rigid portion 25. In the present embodiment, the distal end cover 25a includes a third wire unit insertion hole 63 configuring the wire unit attaching/detaching hole 60, in addition to the above-described distal end opening 6m, an opening 25m for the observation window, and an opening (not shown in the figure) for the illumination window or the like.

Here, the wire unit attaching/detaching hole 60 will be described.

The wire unit attaching/detaching hole 60 is formed by providing the first wire unit insertion hole (abbreviated as a first unit hole, hereinafter) 61, a second wire unit insertion hole (abbreviated as a second unit hole, hereinafter) 62, and the third wire unit insertion hole (abbreviated as a third unit hole, hereinafter) 63.

The first unit hole 61 is a screw hole to which the male screw portion 64m of the lid member 64 formed at the holding frame protrusion portion 32c of the holding frame 32 can be screwed. An inner diameter of the first unit hole 61 is larger than an outer diameter of the distal end portion flange 37f which is a largest outer diameter portion of the rigid shaft portion 37s.

The second unit hole 62 is a screw hole to which a male screw of a sealing screw 65 which is a sealing member formed at a predetermined position of the distal end rigid portion 25 can be screwed. A center axis of the second unit hole 62 is coaxial with the center axis 70a of the wire guide member 70 provided in the image pickup unit 30 arranged inside the through-hole 25h1 for image pickup optics. The inner diameter of the second unit hole 62 is same as or larger than the inner diameter of the first unit hole 61.

The third unit hole 63 is a through-hole fainted at a predetermined position of the distal end cover 25a, and the sealing screw 65 is disposed. On the distal end face of the sealing screw 65, a groove 65g where a distal end of a screwdriver is to be disposed is formed. The groove 65g is a minus-shaped groove or a plus-shaped groove.

The inner diameter of the third unit hole 63 is in a same dimension as the inner diameter of the second unit hole 62 or larger than the inner diameter of the second unit hole 62. A gap between the inner peripheral surface of the third unit hole 63 and the outer peripheral surface of the sealing screw 65 is watertightly retained by applying the adhesive for example.

A center axis of the third unit hole 63 is coaxial with the center axis 70a of the wire guide member 70 provided in the image pickup unit 30 arranged inside the through-hole 25h1 for image pickup optics. Then, the center axis of the third unit hole 63, the center axis of the second unit hole 62, and the center axis of the first unit hole 61 are coaxially arranged.

Here, actions of the endoscope 2 will be described.

According to the endoscope 2 configured as described above, the wire unit 37 arranged inside the wire guide member 70 is pushed and pulled accompanying the operation of the operation lever 24 (see FIG. 1) of the operation portion 10. Then, the moving frame 33 of the image pickup unit 30 is moved forward and backward by pushing and pulling of the wire unit 37, the moving lens 33L is moved between the first position and the second position, and focus adjustment and magnification adjustment are performed.

As long as the wire unit 37 is smoothly moved inside the wire guide member 70, in other words, loosening or disconnection of a wire or the like does not occur in the wire 37w, the moving frame 33 is smoothly moved forward and backward, and the focus adjustment and the magnification adjustment can be surely performed.

In the endoscope 2, for example, in a case that a fault occurs in the focus adjustment, an operator specifies a fault part. For that, the operation portion 10 is disassembled first.

Here, in the case that the operator finds loosening in the wire 37w led out from the proximal end of the guide tube 74 fixed to the operation portion 10 for example, the wire unit 37 is replaced.

Specifically, when the wire unit 37 is to be replaced, the operator first cuts off the distal end side of a loosening part of the wire 37w of the wire unit 37. In addition, the operator detaches the other end portion of the wire 37w from the operation lever 24.

Next, the operator removes the adhesive filling the gap between the inner peripheral surface of the third unit hole 63 and the outer peripheral surface of the sealing screw 65.

Figure 4A:
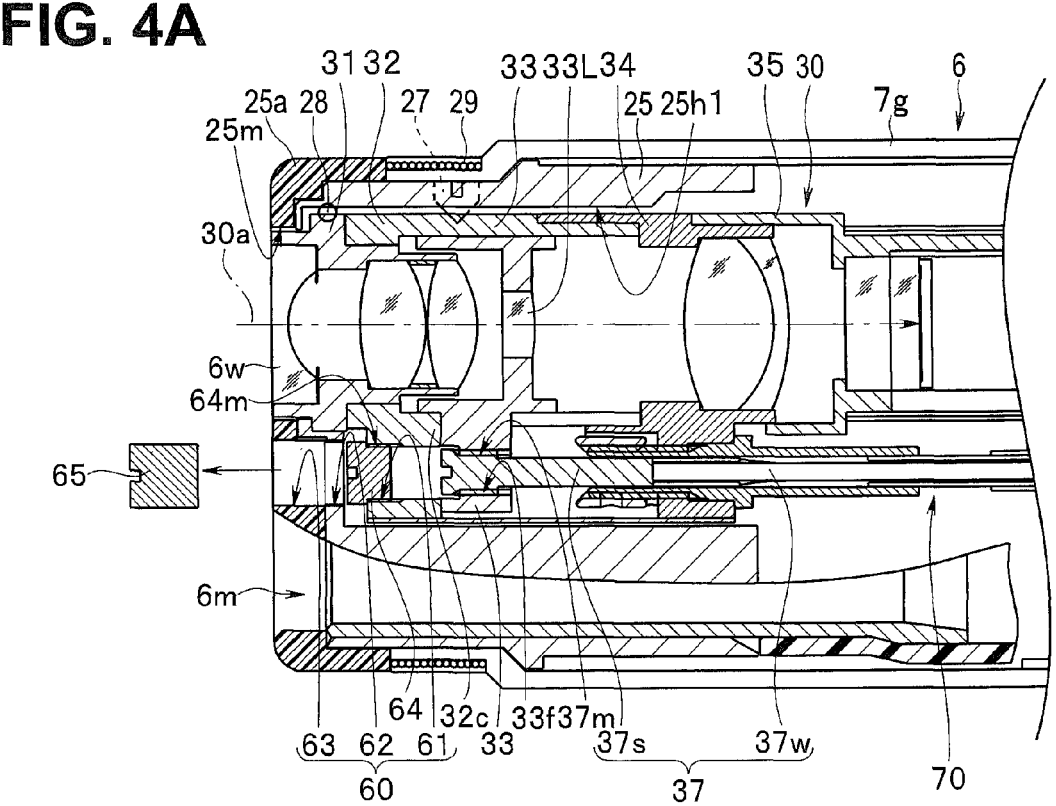
FIG. 4A is a diagram illustrating a state that a sealing screw is detached.

Thereafter, the operator cancels a screwed state of the sealing screw 65 which is screwed to seal the second unit hole 62 provided on the distal end rigid portion 25 by using a tool such as a screwdriver. After cancellation, the operator removes the sealing screw 65 to an outside as illustrated in FIG. 4A.

Figure 4B:
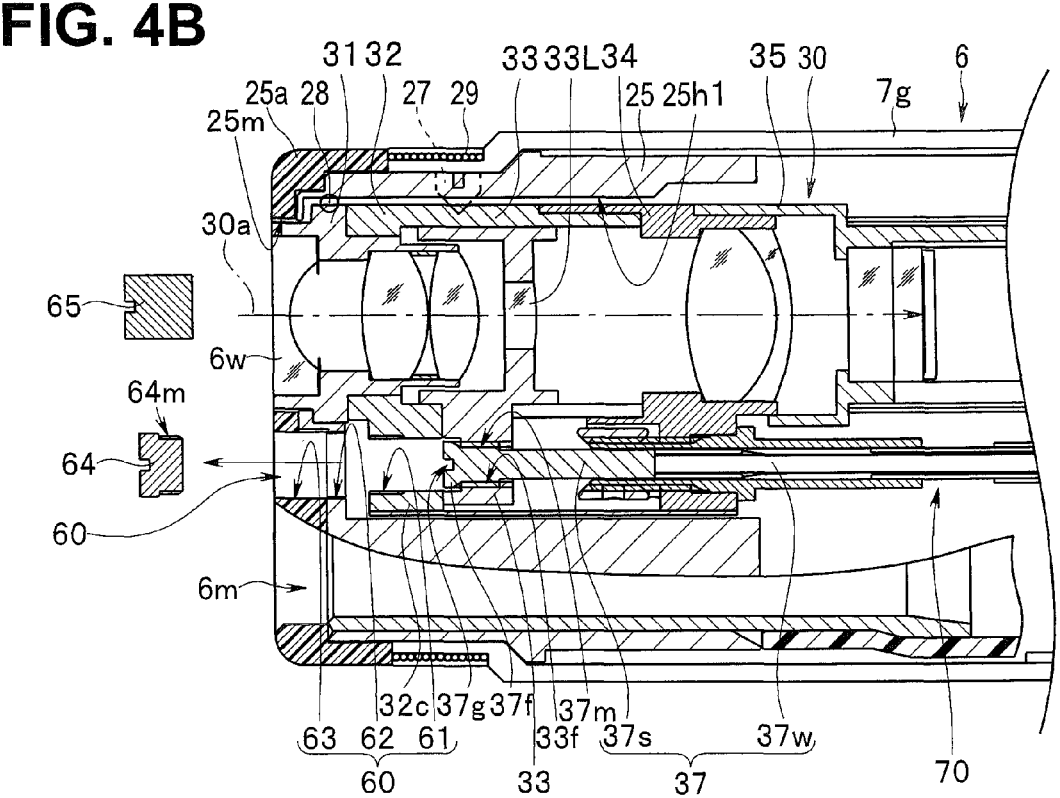
FIG. 4B is a diagram illustrating a wire attaching/detaching hole made to appear at the distal end portion by detaching a sealing screw and a lid member.

Next, the operator cancels the screwed state of the first unit hole 61 provided on the holding frame protrusion portion 32c, and removes the lid member 64 to the outside as illustrated in FIG. 4B.

As a result, at the distal end portion 6, the wire unit attaching/detaching hole 60 configured by the third unit hole 63, the second unit hole 62, and the first unit hole 61 appears. Therefore, the operator can confirm the distal end face of the distal end portion flange 37f provided on the rigid shaft portion 37s of the wire unit 37 and the groove 37g provided on the distal end face, through the wire unit attaching/detaching hole 60.

Here, in order to cancel the screwed state of the rigid shaft portion 37s screwed to the screw hole 33f of the wire unit connecting projection portion 33c, the operator cancels the screwed state by inserting a tool such as a screwdriver to the wire unit attaching/detaching hole 60. After the cancellation, the operator removes the wire unit 37 in the order of the rigid shaft portion 37s and the wire 37w through the wire unit attaching/detaching hole 60.

Figure 5:
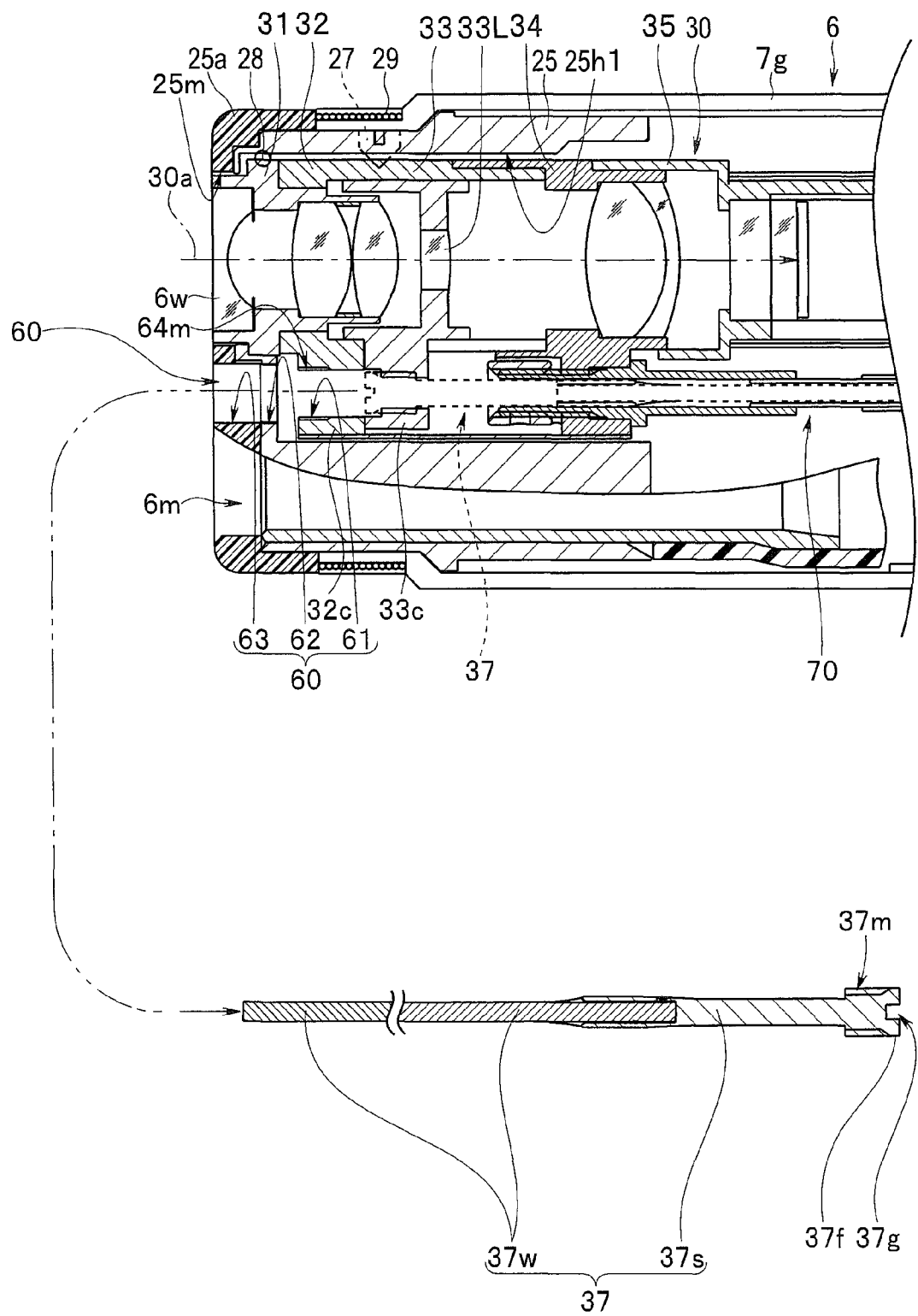
FIG. 5 is a diagram illustrating a state that a wire unit is detached.

As a result, as illustrated in FIG. 5, detachment from the inside of the wire guide member 70 of the wire unit 37 is completed.

Thereafter, the operator starts attaching a new wire unit 37.

Attaching work is a procedure opposite to detaching work, and the operator first inserts the wire 37w of the wire unit 37 to the wire unit attaching/detaching hole 60, and inserts an end portion of the wire 37w into the through-hole 71h of the guide pipe 71 configuring the distal end side of the wire guide member 70.

Thereafter, the operator pushes and advances the wire 37w to a back of the wire guide member 70. That is, the end portion of the wire 37w is inserted into the connection pipe 73 after passing through the inside of the guide pipe 71, inserted into the wire guide tube 74 after passing through the inside of the connection pipe 73, and led out from the end portion of the wire guide tube 74 into the operation portion 10. At the time, as illustrated by a broken line in FIG. 5, the rigid shaft portion 37s passes through the inside of the wire unit attaching/detaching hole 60, and is arranged inside the through-hole 71h of the guide pipe 71.

Here, the operator inserts a tool such as a screwdriver to the wire unit attaching/detaching hole 60, and screws the male screw 37m of the rigid shaft portion 37s to the screw hole 33f of the wire unit connecting projection portion 33c. After the rigid shaft portion 37s is screwed and fixed to the wire unit connecting projection portion 33c, the operator attaches the other end portion of the wire 37w to the operation lever 24.

In addition, the operator screws and arranges the lid member 64 to the first unit hole 61. In addition, the operator screws and arranges the sealing screw 65 to the second unit hole 62, and also applies the adhesive to the gap between the inner peripheral surface of the third unit hole 63 and the outer peripheral surface of the sealing screw 65 to attain a watertightness retaining state.

As a result, the replacement of the wire unit 37 is completed.

In this way, the holding frame protrusion portion 32c configuring the image pickup unit 30 is provided with the first unit hole 61 communicated to the wire unit 37 fixed to the wire unit connecting projection portion 33c of the moving frame 33, the distal end rigid portion 25 is provided with the second unit hole 62, the distal end cover 25a is provided with the third unit hole 63, and the wire unit attaching/detaching hole 60 is configured.

As a result, the wire unit 37 can be easily attached and detached to/from the wire guide member 70 through the wire unit attaching/detaching hole 60.

In addition, by such a configuration that the third unit hole 63 and the second unit hole 62 are sealed by the sealing screw 65 and the first unit hole 61 is closed by the lid member 64, in the case that a fault occurs in the wire 37w of the wire unit 37 inside the operation portion 10, the sealing screw 65 and the lid member 64 are detached without disassembling the side of the insertion portion 9, and the wire unit 37 can be easily and surely attached and detached to/from the wire guide member 70.

Figure 6:
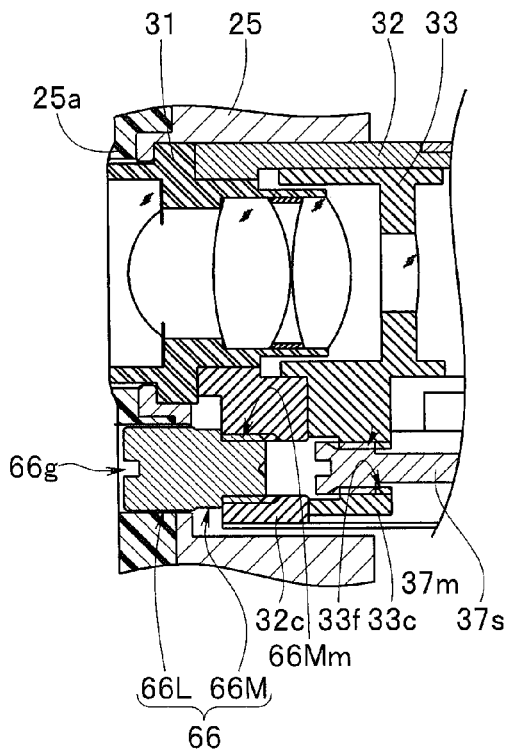
FIG. 6 is a diagram illustrating a sealing lid member for which the lid member and the sealing screw are integrated.

Note that, in the embodiment described above, the sealing screw 65 and the lid member 64 are separate members. However, as illustrated in FIG. 6, the sealing screw 65 and the lid member 64 may configure an integrated sealing lid member 66. The sealing lid member 66 is configured including a large diameter portion 66L and a small diameter portion 66M.

The small diameter portion 66M of the sealing lid member 66 is provided with a male screw 66Mm screwed to a female screw of the first unit hole 61. The large diameter portion 66L of the sealing lid member 66 is arranged inside the second unit hole 62 and inside the third unit hole 63, and the gap between the inner peripheral surface of the third unit hole 63 and the outer peripheral surface of the large diameter portion 66L is watertightly retained with the adhesive. A sign 66g denotes a recessed groove, and the recessed groove is similar to the recessed groove 64g described above.

In this way, by the sealing screw 65 and the lid member 64 configure the integrated sealing lid member 66, the wire unit attaching/detaching hole 60 can be made to appear at the distal end portion 6 of the insertion portion 9 by detaching only one sealing lid member 66. Other actions and effects are similar to the embodiment described above.

Figure 7:
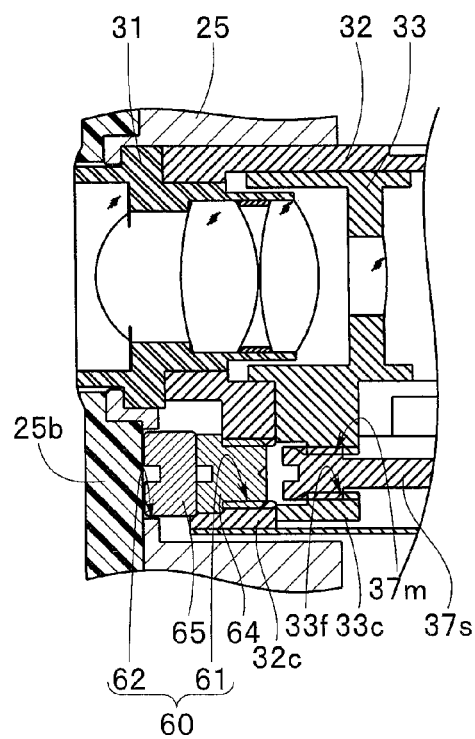
FIG. 7 is a diagram illustrating another configuration example of a distal end cover.

In addition, in the above-described embodiment, the distal end cover 25a is provided with the third wire unit insertion hole 63 configuring the wire unit attaching/detaching hole 60. However, as illustrated in FIG. 7, the configuration may be such that the lid member 64 is screwed and fixed to the second unit hole 62 without providing the third wire unit insertion hole 63 in the distal end cover 25a. In the present embodiment, the wire unit attaching/detaching hole 60 is configured by the first unit hole 61 and the second unit hole 62.

In this way, by a distal end cover 25b for which the third wire unit insertion hole 63 is eliminated from the distal end cover 25a, when the wire unit 37 is to be replaced, time and labor of detaching the distal end cover 25b from the distal end rigid portion 25 arise. However, after the replacement of the wire unit 37 is completed, by attaching the distal end cover 25b to the distal end rigid portion 25, the watertightness can be substantially improved compared to the case of turning the third unit hole 63 to the watertightness retaining state with the adhesive.

Figure 8:
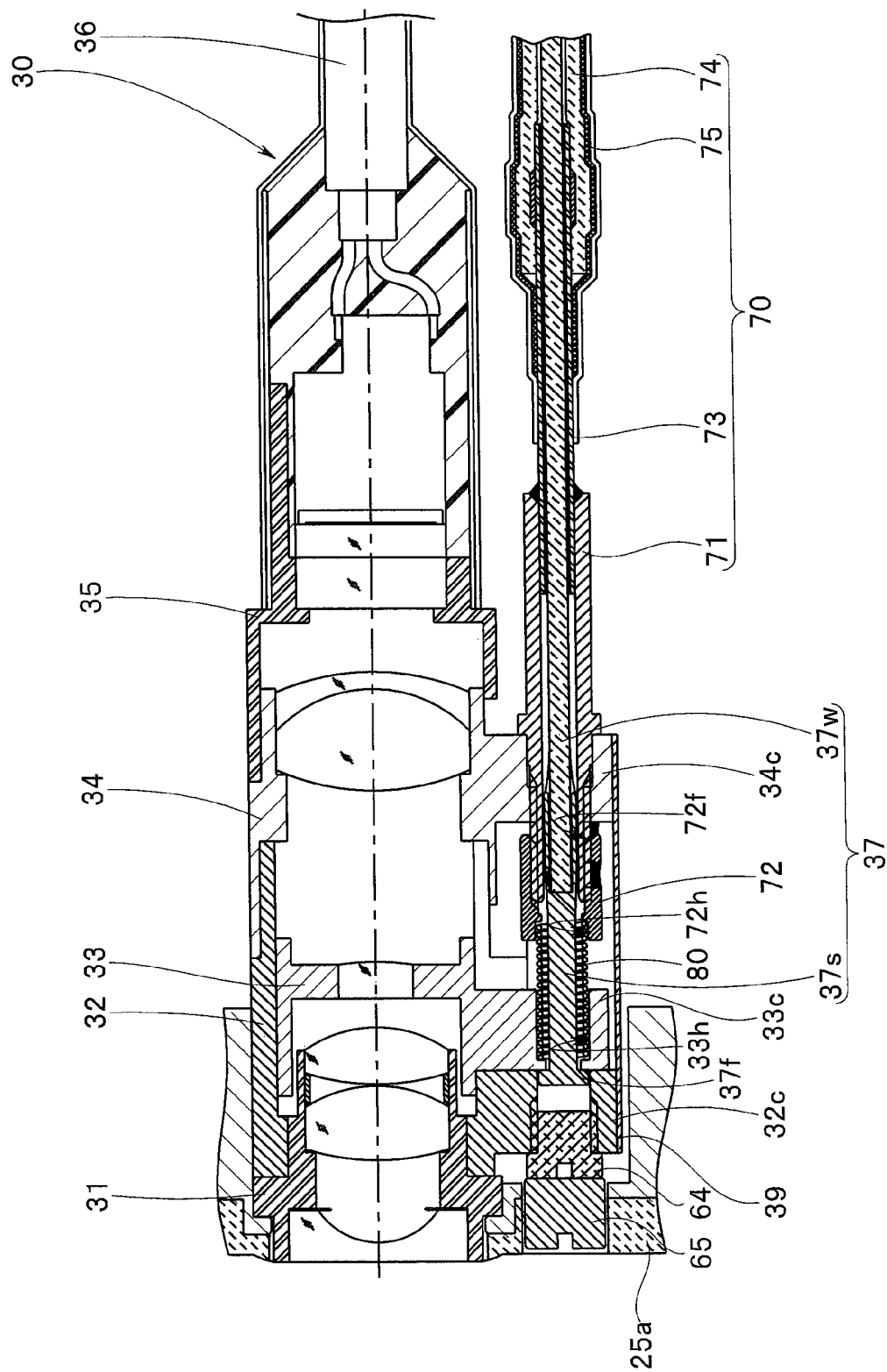
FIG. 8 is a diagram illustrating a configuration example in which a moving frame is arranged at a first position by a coil spring.

Note that, as illustrated in FIG. 8, by attaining the configuration of pressing the moving frame 33 to the first position by a coil spring 80, the rigid shaft portion 37s of the wire unit 37 can be attached without being screwed to the wire unit connecting projection portion 33c.

As a result, after the wire unit attaching/detaching hole 60 is made to appear at the distal end portion 6 of the insertion portion 9, the wire unit 37 can be replaced without need of work of canceling screwing of the rigid shaft portion 37s and work of screwing the rigid shaft portion 37s.

In the configuration, one end portion of the coil spring 80 is arranged inside a recessed portion 33h including a distal end seat provided in the wire unit connecting projection portion 33c, and the other end portion is arranged inside a recessed portion 72h including a proximal end seat provided in the adjustment ring 72.

The coil spring 80 is turned to a predetermined contracted state in the state of operating the operation lever 24 and arranging the moving frame 33 at the second position.

The invention described in the individual embodiments above is not limited to the embodiments and modifications and can be variously modified without departing from the scope in an implementation phase in addition. Further, the embodiments described above include the inventions in various stages, and various inventions can be extracted by appropriate combinations in a plurality of disclosed constituent elements.

For example, even when some constituent elements are deleted from the entire constituent elements indicated in the embodiments, in the case that the problem to be solved by the invention can be solved and the effect described in the effect of the invention can be obtained, the configuration from which the constituent elements are deleted can be extracted as the invention.

According to the present invention, the endoscope which allows the replacement of only the wire unit included in the configuration of the image pickup unit without disassembling the distal end portion of the endoscope insertion portion can be realized.

What is claimed is:

1. An endoscope comprising:
   an endoscope distal end rigid member;
   an objective optical system fixing frame configured to hold an optical member configuring an objective optical system arranged on a distal end side inside a through-hole formed along a longitudinal axis of the endoscope distal end rigid member;
   a moving frame arranged on a holding frame freely movably forward and backward and configured to hold a moving lens such that the moving lens is moved forward and backward along an optical axis of the objective optical system;
   a wire unit including an operation wire, one end portion of which is connected to an operation lever, and a rigid shaft portion configured such that another end portion of the operation wire is integrally fixed to one end face side, a diameter of the rigid shaft portion being larger than the operation wire;

a wire unit connecting projection portion provided protruding outward from an outer peripheral surface of the moving frame, and configured such that a flange provided on another end face side of the rigid shaft portion and having a diameter larger than the rigid shaft portion is screwed to a distal end face side;

a first wire unit insertion hole provided on a holding frame protrusion portion including a proximal end face to which a distal end face of the wire unit connecting projection portion protruding outward from an outer peripheral surface of the holding frame comes into contact, and configured to be a through-hole through which a flange of the rigid shaft portion can pass in a state that screwing to the wire unit connecting projection portion is canceled;

a lid member attached to the first wire unit insertion hole;

a second wire unit insertion hole formed along the longitudinal axis of the endoscope distal end rigid member, configured to be coaxial with a center axis of the first wire unit insertion hole, and configured to be a through-hole through which the flange of the rigid shaft portion can pass in the state that screwing to the wire unit connecting projection portion is canceled; and a sealing member configured to seal the second wire unit insertion hole.

2. The endoscope according to claim 1, wherein an inner diameter of the second wire unit insertion hole is same as or larger than an inner diameter of the first wire unit insertion hole.

3. The endoscope according to claim 1, wherein the rigid shaft portion of the wire unit is fixed to the wire unit connecting projection portion by screwing, the lid member is fixed to the holding frame protrusion portion by screwing, and the sealing member is fixed to the endoscope distal end rigid member by screwing.

4. The endoscope according to claim 1, wherein the lid member and the sealing member are integrally configured.

5. The endoscope according to claim 1, wherein a distal end cover member disposed to cover a distal end face side of the endoscope distal end rigid member is provided with a third wire unit insertion hole which is a through-hole configured to be coaxial with a center axis of the second wire unit insertion hole and have a diameter same as or larger than a diameter dimension of the second wire unit insertion hole.

* * * * *